United States Patent [19]

Ahmad

[11] Patent Number: 4,820,039
[45] Date of Patent: Apr. 11, 1989

[54] MEDICAL APPARATUS FOR DIAGNOSING EYE CONDITIONS

[76] Inventor: Riyaz Ahmad, 9 Melrose Grove, Spinneyfield, Rotherham S60 3NA, England

[21] Appl. No.: 117,821

[22] Filed: Nov. 9, 1987

[30] Foreign Application Priority Data

Mar. 11, 1986 [GB] United Kingdom ............... 8626188

[51] Int. Cl.$^4$ .......................... A61B 3/10; A61B 3/14
[52] U.S. Cl. .................................. 351/212; 351/206; 354/6
[58] Field of Search ............... 351/212, 247, 206, 207, 351/208; 354/62

[56] References Cited

U.S. PATENT DOCUMENTS

| | | |
|---|---|---|
| 1,119,273 | 12/1914 | Gowlland .................... 351/212 |
| 1,918,540 | 7/1933 | Hartinger .................... 351/212 |
| 3,169,459 | 2/1965 | Friedberg et al. ............ 351/212 |
| 3,640,610 | 2/1972 | Nupuf ........................ 351/212 |
| 3,797,921 | 3/1974 | Kilmer et al. ............... 351/212 |
| 3,804,528 | 4/1974 | Kilmer et al. ............... 351/212 |

*Primary Examiner*—Rodney B. Bovernick
*Attorney, Agent, or Firm*—Cushman, Darby & Cushman

[57] ABSTRACT

Medical apparatus, a non contact measuring device, for use in diagnosing and monitoring various eye conditions, the apparatus including a camera having in the plane of the image a transparent screen carrying a grid or other markings which will become reproduced on a photograph or transparency of the patient's eye. The camera will preferably have a disc of circles on its lens so that the user of the apparatus will be able to observe the reflections of the rings on a patient's cornea.

5 Claims, 3 Drawing Sheets

MEDICAL APPARATUS FOR DIAGNOSING EYE CONDITIONS

FIELD OF THE INVENTION

The invention relates to medical apparatus and more particularly to apparatus for use in diagnosing and monitoring various eye conditions.

Eye specialists in their day to day clinical practice need to measure various features of a patient's eyes. For example, they need to measure the size of the eye and its various parts, that is the pupil and the cornea. They also need to measure the degree of protrusion of the eye and the degree of drooping of the eyelid resulting from various diseases. Also any lesions or tumours on the eye, or iris or on the eyelid. They need to be able to monitor such abnormalities, that is to say check on any changes from time to time so that it can be determined whether a certain condition is improving or getting worse. Distance between two eyes or pupils is needed to be measured, as is the curvature of cornea.

Various instruments and devices have been used heretofore for the purpose of determining and monitoring various opthalmic measurements, ranging from rulers and callipers to expensive instruments.

The exact radius of curvature of a patient's cornea may be obtained by the use of the so-called Donaldson Photokeratograph. In this device, the original photograph of the cornea is compared with a graph. Various expensive keratographs are in use, the photographs being analysed by computer in some of these. Another instrument is the so-called Keratometer which is a short distance compound telescope with a device for measuring by the method of "doubling". However, all such known instruments are relatively expensive and almost always involve direct contact with the eye or working at close proximity to the eye so that this has either caused difficulties due to the patient blinking, particularly where the patient has been a baby or young child, or has necessitated the patient being anaesthetised. To my knowledge no accurate nontouch method is available for measuring distance between two eyes or pupils (P.D. measurement) and sideward displacement of the eye-ball. Also the size of any lesion or tumour on eye or on iris cannot be measured accurately with patient lying down or child in mother's lap. A further difficulty is that known devices, for example for measuring the protrusion of the eye, are not completely satisfactory in use because they are frequently found to give different readings in the hands of different users. Devices for measuring the depth of the anterior chamber of the eye, that is to say the space between the outer transparent coat of the eye and the colored iris, are difficult to use and in fact for this reason are hardly ever used in normal clinical practice.

SUMMARY OF THE INVENTION

According to the invention, photographic apparatus for use in diagnosing and monitoring various eye conditions, includes a camera having in the plane of the image a transparent screen carrying a grid or other markings which become reproduced on a photograph or transparency, the arrangement being such that when a photograph or transparency of a patient's eye has been produced, various dimensions of the features of the eye can be determined by reference to the grid the spacing of the lines of which are known. The camera may have a disc of circles on its lens whereby the user of the apparatus is able to observe the reflections of the rings on a patient's cornea and whereby the circles are reproduced on a photograph or transparency in addition to the grid or other markings in the plane of the image within the camera. The disc of circles may be a push fit on the lens. The disc of circles may have a series of discontinuous apertures which define the series of circles. Alternatively, the disc may have a reflective surface with a series of painted circles or may have a dark background with a series of circles painted on in a white paint.

DESCRIPTION OF THE PREFERRED EMBODIMENT

Figure 1:
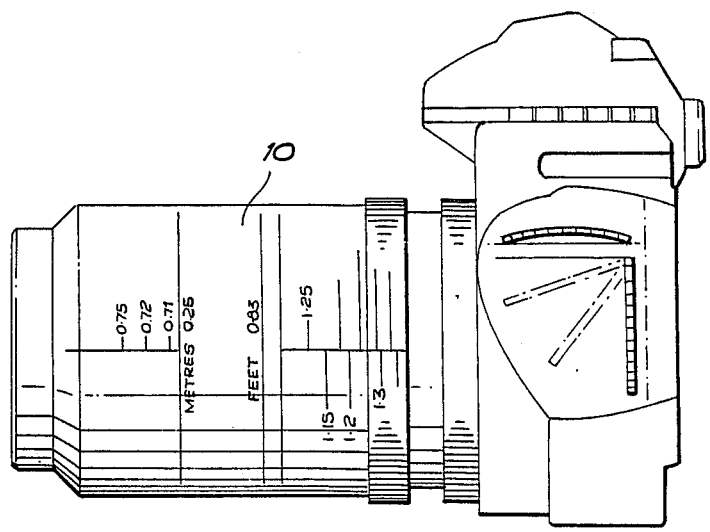
FIG. 1 is a partly broken away side view of a 35 mm single lens reflex photographic camera embodying the invention.
Figure 2:
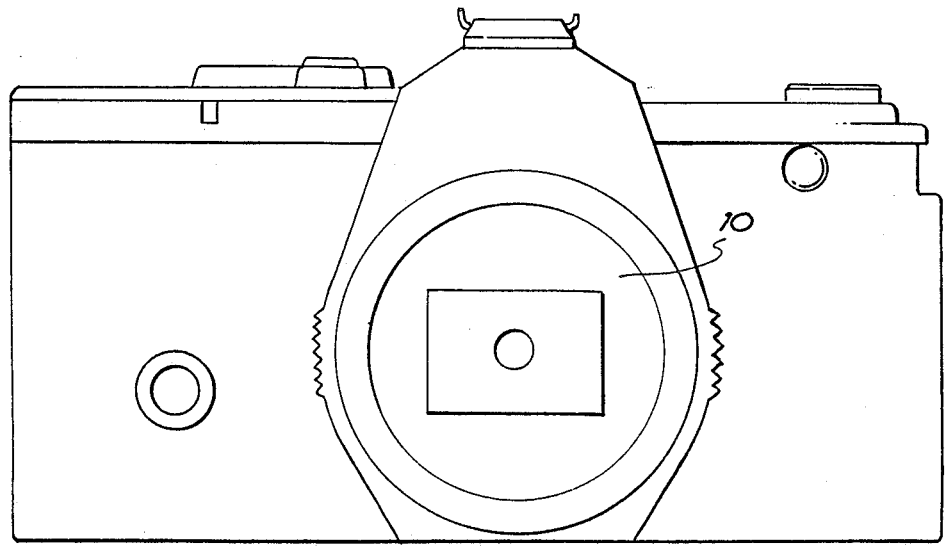
FIG. 2 is a front view of the body of the SLR camera.

Referring now to FIGS. 1 and 2 of the drawings, the photographic camera there illustrated is a single lens Reflex camera provided with a type of lens 10 of which the magnification can be adjusted at 1:1, that is to say life size, or 1:2 (half life size) and so on. When the required magnification has been brought about by the adjustment of the lens, an adjustment to form a clear image of a patient's eye at the view-finder is made by moving the camera bodily. A simple slide rail mounting (not shown) is used to carry out this focussing adjustment.

Figure 3:
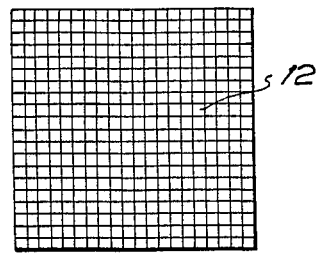
FIG. 3 is a view of one of a pair of transparent screens fitted within the camera one on the viewfinder screen and the other behind the shutter screen, i.e. in front of the filmplane.

Referring now to FIG. 3, the transparent screen 12 there illustrated is made of glass or plastic or of a negative film and is marked, as shown, with a grid of fine lines, the lines in both planes being at 2 m.m. spacing.

Figure 4:
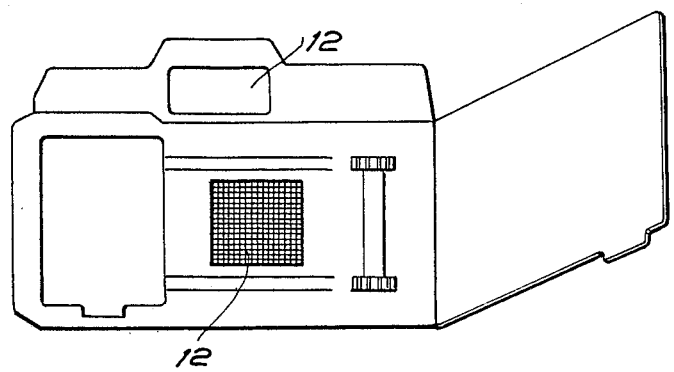
FIG. 4 is a view of the camera with the back open, showing the fitment of the transparent screen within the camera, i.e. behind the shutter screen.

A screen as illustrated in FIG. 3 is fixed in position in place of the normal focussing screen of the camera (see FIG. 1). A similar screen is fixed in position behind the shutter screen as shown in FIGS. 1 and 4.

Figure 5:
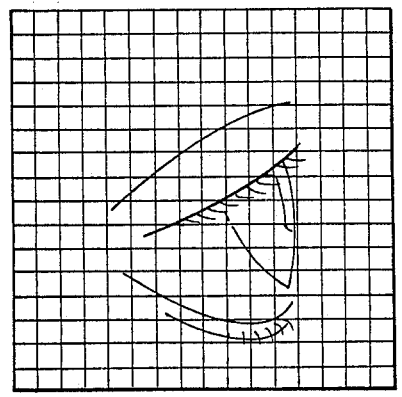
FIGS. 5 and 6 are views which show the user's view of a patient's eye through the view-finder screen, and of course the subsequent photographic print or transparency.
Figure 6:
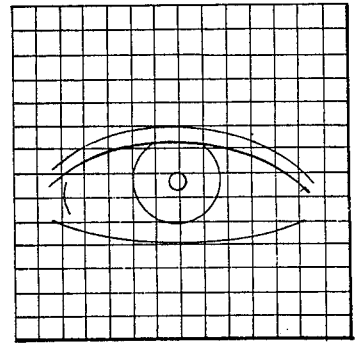

In use of the apparatus, the camera on the slide mounting referred to will be fixed on some convenient stand or table and the patient will be seated with his or her chin resting on a rest to keep the head stable, this being especially important in the case of an elderly patient. The arrangement is such that when the modified camera is used by an eye specialist, the user's view of the patient's eye being either from the side or front as shown in FIGS. 5 and 6 respectively, the grid of the viewfinder is superimposed on the view of the eye, and from this precise measurements of the eye can be taken.

In addition, if an exposure is made, the resulting photographic print or transparency will have such a grid extending across the view of the eye. From this, the size of any particular part of the eye, in the condition in which it then was, can be scaled off precisely. Alternatively, the degree by which the eye protruded at that time, or the degree of drooping of the eyelid at that time, can subsequently be measured.

It will be understood that by the use of the photographic apparatus referred to it is a simple matter to monitor any particular eye condition, that is to say take a series of similar photographs at intervals and to note any changes taking place. The great advantage of using apparatus embodying the invention in diagnosing or monitoring various eye conditions in this way is that the apparatus is easily portable and can be used without touching the patient's eye or face and this is especially important when the patient is a baby or young child. Another advantage is that the apparatus can be used with repeatable accuracy and the fact that identical results can be obtained by different users. The invention may also be of use in connection with the fitting of contact lenses.

POSSIBLE MODIFICATIONS

Various modifications may be made. For example, spacing of the fine lines of the grid may be varied, but a 2 m.m. spacing of the lines has been found to be ideal for general use. It will also be understood that the grid need not necessarily be made up of horizontal and vertical lines. For example, in some instances it may be more useful for the transparent screen to be marked with a network of fine lines some of which are radiating lines and some of which describe circles of different radii around a central point. Indeed, it is not essential for the markings on the transparent window to be in the form of fine lines. They could be provided in the form of a series of dots at such spacings that a user of the apparatus can look through the viewfinder of the camera and determine by direct reference with the markings referred to the size (or change in size) of any feature or abnormality of a patient's eye.

Figure 7:
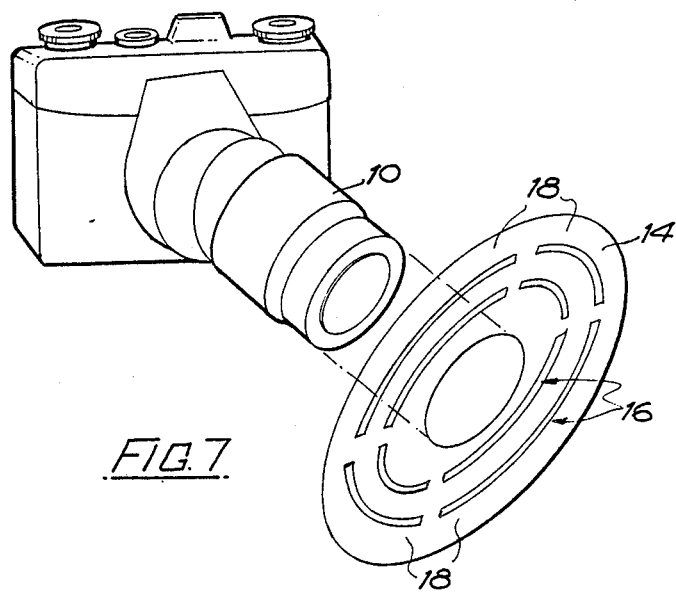
FIG. 7 is a perspective view which illustrates additional apparatus which will be referred to, and FIG. 8 is a view similar to FIG. 6 which shows the user's view through the view-finder of the camera and/or the photograph with the additonal apparatus referred to in use.

In FIG. 7 there is illustrated the use of a further item of apparatus in conjunction with the apparatus described above, this being a circular disc 14 which can be fitted as shown on the lens 10 of the camera. As shown, the disc 14 is provided with a series of concentric circles 16 of varying sizes, the purpose of which is to cause a reflection of the circles to appear on the cornea of a patient whose eye is observed through the viewfinder. (In the illustrated example the disc 14 is shown to have a pair of such circles but it could have three or more such circles if preferred). The series of circles will of course also appear on a photographic print or transparency. Since the distance between the series of circles 16 is a known constant, if there is any variation or distortion of their reflections in the eye specialist's view of the eye or on the photographic print or transparency the skilled eye specialist can deduce the degree of abnormality of the patient's eye which this indicates. It will of course be understood that in a perfectly healthy eye the series of reflectd circles will be perfectly round and equally spaced. Any distortion from the perfectly round can be measured quite easily with reference to the lines of the grid.

Figure 8:
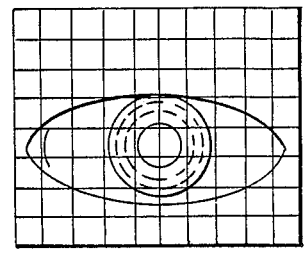

The user's view through the viewfinder of the camera, or photographic print or negative, as the case may be, with the additional apparatus referred to in use, is shown in FIG. 8. The reflections of the two concentric circles of the disc 14 are represented by the chain-dotted circles. As previously mentioned, an abnormality of a patient's eye may be indicated by a variation or distortion in the reflections of the two concentric circles. In other words, the circles may appear to be out of round. In addition to this, however, a skilled eye specialist will be able to deduce the radius of curvature of the eye. This is because the patient's cornea reflects the circles of the disc 14 in the manner of a convex mirror. Consequently, the more convex the cornea the smaller will be the size of the reflected circle or circles. Conversely, the less convex the cornea the larger will be the size of the reflected circle or circles. The exact size of the or each reflected circle can very easily be observed by the eye specialist when viewing the eye through the apparatus, or when studying a photographic print or transparency, with reference to the lines of the grid or other markings the spacings of which are known.

The disc 14 which is illustrated in FIG. 7 has been made of thick cardboard and has a series of cut out discontinuous apertures 18 which define the series of circles 16. However, it will be understood that the disc could be made in various different ways and of other materials. It could for example have a reflective surface with a series of painted circles. Alternatively, it could be made of a dark coloured material with a series of circles painted on in a white paint for example.

Additional convex lenses could be fitted in front of the lens 10 to magnify the view of the eye. The apparatus may include means for illuminating the patient's eye and/or the disc 14 of circles which are to be reflected in the patient's cornea. Conventional ring or other flashes are used when necessary.

What I claim and desire to secure by letters patent is:
1. A photographic apparatus for use in diagnosing an monitoring various conditions of the eye comprising:
   a camera;
   a transparent screen mounted in a plane of said camera in which an image is produced, said transparent screen having uniform markings thereon with known spaces therebetween so that said markings are reproduced on a photograph or transparency of an image produced by the camera and so that when a photograph or transparency of a patient's eye has been produced, dimensions of the features of the eye can be determined with reference to the uniform markings;
   a disc of circles mounted on a lens of the camera for producing reflections of the circles on a patient's cornea so that the circles are reproduced on a photograph or transparency of an image produced by within the camera.

2. A photographic apparatus according to claim 1, wherein the disc of circles is mounted to the lens by push fitting the disc on the lens.

3. A photographic apparatus according to claim 1, wherein said circles on said disc are defined by a series of discontinuous apertures in the disc.

4. A photographic apparatus according to claim 1, wherein said disc has a reflective surface with a series of circles painted thereon.

5. A photographic apparatus according to claim 1, wherein said disc has a dark background with a series of circles painted thereon in white paint.

* * * * *